United States Patent [19]

Ogata et al.

[11] Patent Number: 4,612,322
[45] Date of Patent: Sep. 16, 1986

[54] AZOLE TYPE DIOXOLANE DERIVATIVES

[75] Inventors: Masaru Ogata, Hyogo; Hiroshi Matsumoto, Osaka; Shiro Kida, Osaka; Katsuya Tawara, Osaka, all of Japan

[73] Assignee: Shionogi & Co., Ltd., Osaka, Japan

[21] Appl. No.: 632,852

[22] Filed: Jul. 20, 1984

[30] Foreign Application Priority Data

Jul. 20, 1983 [JP] Japan ................ 58-133040

[51] Int. Cl.⁴ ........... A01N 43/50; A01N 43/653; C07D 405/06; A61K 31/41
[52] U.S. Cl. ................ 514/383; 548/262; 548/336; 548/341; 549/548; 568/331; 568/332; 568/333; 568/335; 568/337
[58] Field of Search ........... 548/262, 336; 514/383, 514/397

[56] References Cited

FOREIGN PATENT DOCUMENTS

| 0094167 | 11/1983 | European Pat. Off. | 548/262 |
| 0128383 | 7/1983 | Japan | 548/262 |
| 2095236 | 9/1982 | United Kingdom | 548/262 |

*Primary Examiner*—Alton D. Rollins
*Attorney, Agent, or Firm*—Wenderoth, Lind & Ponack

[57] ABSTRACT

A compound of the formula:

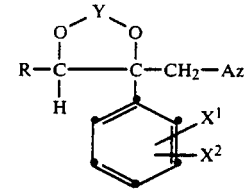

(wherein
Az is imidazolyl or triazolyl;
R is $C_1$-$C_5$ alkyl or phenyl optionally substituted by 1 to 3 members selected from halogen, $C_1$-$C_5$ alkyl, and $C_1$-$C_5$ alkoxy;
$X^1$ and $X^2$ each is hydrogen, halogen, $C_1$-$C_5$ alkyl, or $C_1$-$C_5$ alkoxy;
Y is C=O, C=S, S=O, or $R^1$—C—$R^2$; and
$R^1$ and $R^2$ each is hydrogen, $C_1$-$C_3$ alkyl or, taken together may form $C_4$-$C_6$ alkylene)

or its acid addition salt being useful as an antimycotic agent is prepared by reacting a corresponding diol with a cyclizing agent.

8 Claims, No Drawings

AZOLE TYPE DIOXOLANE DERIVATIVES

The present invention relates to azole type dioxolane derivartives. More particularly, this invention relates to compounds of the formula:

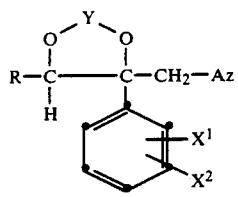

(wherein
  Az is imidazolyl or triazolyl;
  R is $C_1$-$C_5$ alkyl or phenyl optionally substituted by 1 to 3 members selected from halogen, $C_1$-$C_5$ alkyl and $C_1$-$C_5$ alkoxy;
  $X^1$ and $X^2$ each is hydrogen, halogen, $C_1$-$C_5$ alkyl, or $C_1$-$C_5$ alkoxy;
  Y is C=O, C=S, S=O, or $R^1$—C—$R^2$; and
  $R^1$ and $R^2$ each is hydrogen, $C_1$-$C_3$ alkyl, or $R^1$ and $R^2$ taken together may form $C_4$-$C_6$ alkylene)
or an acid addition salt thereof, said compounds being useful as antimycotic agents.

The meanings of the terms used in the above definitions are explained below: the $C_1$-$C_5$ alkyl illustratively includes methyl, ethyl, propyl, isopropyl, butyl, t-butyl, and pentyl; the $C_4$-$C_6$ alkylene includes tetramethylene, pentamethylene, or hexamethylene; the $C_1$-$C_5$ alkoxy illustratively includes methoxy, ethoxy, propoxy, isopropoxy, butoxy, isobutoxy, and pentyloxy; the halogen includes fluorine, chlorine, bromine, and iodine; and the triazolyl represented by Az includes 1H-1,2,4-triazol-1-yl and 4H-1,2,4-triazol-4-yl.

Ketoconazole (U.S. Pat. Nos. 4,144,346 and 4,223,036) has already been used practically as an oral antimycotic agent in Europe and U.S.A., while some adverse reactions thereof such as hepatic dysfunction have been reported. Further some azole type dioxolane derivatives have been proposed but their utility is mainly directed to agricultural fungicides [U.K. Unexamd. Pat. Publn. Nos. 2,095,236; and 2,124,208]. The present inventors found that novel azole type dioxolane derivatives (I) show potent antimycotic activity when administered orally.

The objective compounds (I) are prepared according to the following reaction sequence.

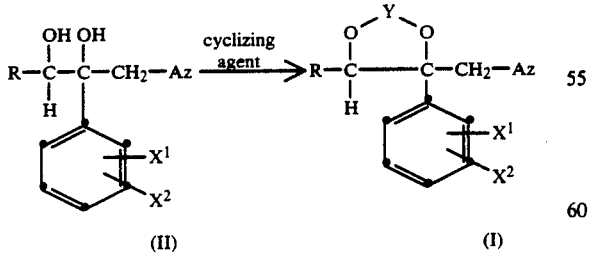

(wherein Az, R, $X^1$, $X^2$ and Y each has the same significance as defined above.)

The objective compound (I) can be provided by reacting the starting material (II) with a cyclizing agent. Examples of cyclizing agents are imidazoles such as 1,1'-carbonyldiimidazole or 1,1'-thiocarbonyldiimidazole, thionyl halides such as thionyl chloride or thionyl bromide; phosgenes such as phosgene or thiophosgene; oxalyl chloride; a dihalomethane such as bromochloromethane or dibromomethane; a halocarbonic acid ester such as ethyl chlorocarbonate or phenyl chlorocarbonate; and a ketone such as acetone, methyl ethyl ketone, diethyl ketone, ethyl propyl ketone, dipropyl ketone, cyclopentanone, cyclohexanone or cycloheptanone/its dimethyl ketal. For preparation of the ketal (I): (Y=$R^1$—C—$R^2$; $R^1$, $R^2$=$C_1$-$C_3$ alkyl or taken together $C_4$-$C_6$ alkylene), the reaction may be performed by using a ketone and its dimethyl ketal as a cyclizing agent in the presence of a Lewis acid such as zinc chloride, aluminum chloride or calcium chloride under heating up to the boiling point of the solvent used. If necessary, an acid such as p-toluenesulfonic acid or hydrochloric acid may be incorporated for acceleration. This reaction may be carried out in an appropriate solvent (e.g., chloroform, carbon tetrachloride, 1,2-dichloroethane, methylene chloride, dimethylformamide, benzene, or toluene) if necessary, in the presence of a base (e.g., sodium hydride, triethylamine, pryidine, 2,6-lutidine, or γ-picoline) at a temperature of about 15° C. to about 130° C., preferably at room temperature to the boiling point of the solvent.

Since the compounds (I) contain two or three asymmetrical carbons, they are generally prepared as a mixture of diastereomers which can be separated into the respective diastereomers in a conventional manner.

The starting materials (II) can be prepared, for example, according to the following reaction sequence.

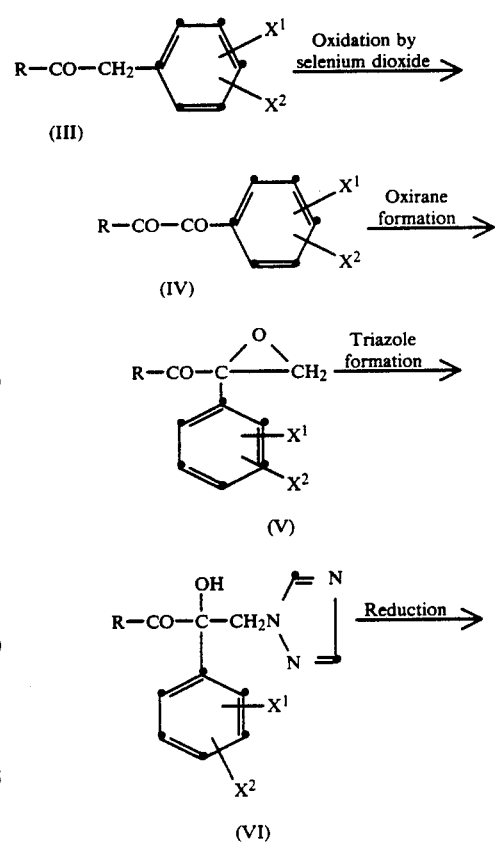

-continued

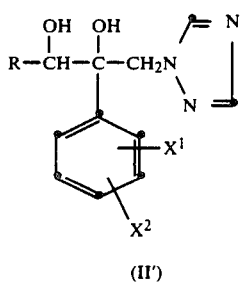

(II')

(UK. Pat. Appln. No. 8,404,426)

(wherein R, $X^1$, $X^2$, and Y each has the same significance as defined above).

Preferred compounds of the objective compounds (I) are represented by the formula:

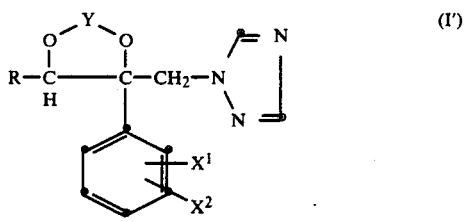

(wherein R is $C_3$–$C_4$ alkyl or phenyl substituted by 1 or 2 halogen atoms; at least one of $X^1$ and $X^2$ is halogen; and Y is C=O, C=S, S=O or $CH_2$)

The objective compounds (I) provided in the above step can be converted into pharmaceutically acceptable acid addition salts thereof. Examples of the acids which can form these salts are organic acids such as acetic acid, citric acid, tartaric acid, malic acid, succinic acid, malic acid, fumaric acid, and methanesulfonic acid and inorganic acids such as hydrohalogenic acids, sulfuric acid, and phosphoric acid.

The objective compounds (I) or their salts show potent antimycotic activity and are useful as antimycotic agents for medical or veterinary use. Particularly, the objective compounds (I) are useful as oral or injectable antimycotic agents.

The objective compounds (I) or their pharmaceutically acceptable acid addition salts can be used alone or together with additives such as carriers, excipients, diluents, dispersants and the like in the dosage forms for internal or external use. These dosage forms includes solutions, suspensions, powders, pills, granules, capsules, tablets, injections, ointments, tincture, suppositories, and the like; and these preparations can be prepared in a conventional manner for formulation. This compound (I) can be administered orally to a human adult at a dose or doses of about 10–2,000 mg per day.

Furthermore, the objective compounds (I) or their acid addition salts can be expected to be fungicides when used agriculturally for crops such as fruit trees, rice, wheat, cotton, corn, soya bean, and the like.

The present invention will be explained in detail by the following Examples.

EXAMPLE 1

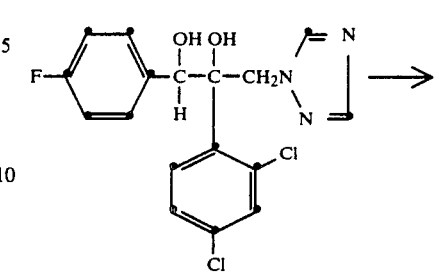

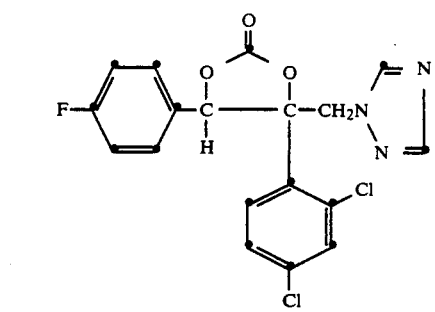

A mixture of 500 mg of 2-(2,4-dichlorophenyl)-1-(4-fluorophenyl)-3-(1H-1,2,4-triazol-1-yl)-1,2-propanediol, 530 mg of 1,1'-carbonyldiimidazole and 10 ml of dry chloroform is heated under reflux for 1 hour. Water is added to the reaction mixture, and the chloroform layer is separated, dried over anhydrous sodium sulfate, and concentrated. The residue is chromatographed on a column of silica-gel and eluted with a mixture of methylene chloride and methanol (100:0–98:2 v/v). The eluate is concentrated, and the residue is crystallized from ethyl acetate-isopropyl ether to give 420 mg of 4-(2,4-dichlorophenyl)-5-(4-fluorophenyl)-2-oxo-4-(1H-1,2,4-triazol-1-yl)methyl-1,3-dioxolane as crystals. m.p. 191°–192° C. Yield: 78.7%

Anal. Calcd. (%) (for $C_{18}H_{12}N_3O_3Cl_2F$): C, 52.96; H, 2.96; N, 10.29; Cl, 17.37; F, 4.65. Found (%): C, 53.35; H, 3.15; N, 10.42; Cl, 17.34 F, 4.84.

IR $\nu_{max}^{Nujol}$ 1810 cm$^{-1}$ (C=O).

NMR $\delta^{CDCl_3}$ 4.08(d, J=15Hz,1H) ⎫
4.93(d, J=15Hz,1H) ⎬ —CH$_2$—

6.08(s, 1H, —O—CH⟨ ), 7.03–7.90 (m, 9H, arom.H)

EXAMPLE 2-15

The following starting materials (II') are allowed to react with 1,1'-carbonyldiimidazole in the same manner as in Example 1 to give the corresponding objective compounds (Ia).

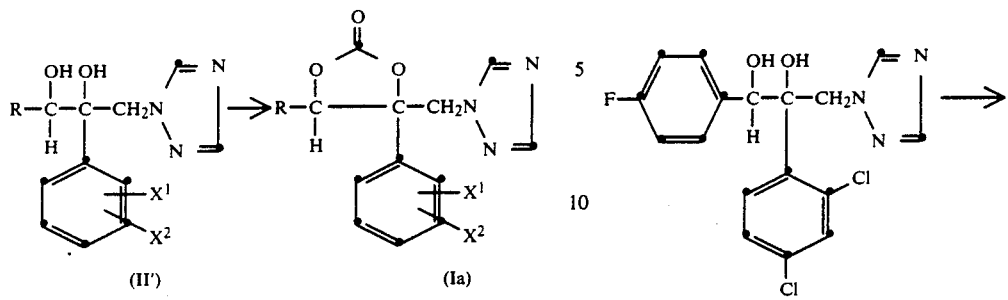

(II')  (Ia)

| Ex. No. | R | X¹ | X² | m.p. (°C.) | Yield (%) |
|---|---|---|---|---|---|
| 2 | i-Pr | 2-Cl | 4-Cl | 150–150.5 | 52.3 |
| 3 | Ph | 2-Cl | 4-Cl | 138–139 | 34.3 |
| 4 | Bu | 2-Cl | 4-Cl | 137–138 | 42.3 |
| 5 | 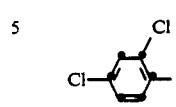 3,4-Cl₂-C₆H₃ | 4-Cl | H | 162–163 | 78.2 |
| 6 | 2,3-Cl₂-C₆H₃ | 2-Cl | 4-Cl | 222–223 | 64.4 |
| 7 | 2-Cl-C₆H₄ | 2-Cl | H | 234–235 | 93.4 |
| 8 | 4-F-C₆H₄ | 4-F | H | 81–82 | 69.4 |
| 9 | 4-Cl-C₆H₄ | 4-Cl | H | 155–156 | 70.1 |
| 10 | 2-Cl-C₆H₄ | 3-Cl | H | 148.5–149.5 | 57.9 |
| 11 | 4-CH₃-C₆H₄ | 4-CH₃ | H | 139–140 | 79.6 |
| 12 | Pr | 2-Cl | 4-Cl | 179–180 | 70.1 |
| 13 | Pr | 4-Cl | H | 121–122 | 69.0 |
| 14 | Ph | 2-Cl | H | 220–222 | 20.4 |
| 15 | 4-CH₃-C₆H₄ | 2-Cl | H | 195–196 | 26.0 |

Note:
Abbreviations in the table each has the following meaning.
Ph(Phenyl), Pr(n-propyl), i-Pr(isopropyl), Bu(n-butyl).

EXAMPLE 16

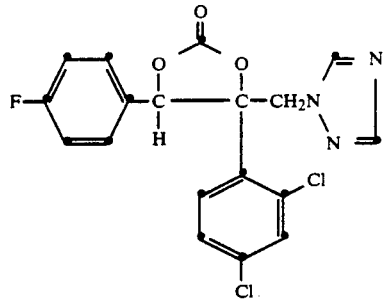

To a solution of 400 mg of 2-(2,4-dichlorophenyl)-1-(4-fluorophenyl)-3-(1H-1,2,4-triazol-1-yl)-1,2-propanediol and 430 mg of triethylamine in 20 ml of dry chloroform is added a solution of 532 mg of oxalyl chloride and 2 ml of dry chloroform in small portions with ice-cooling, and the mixture is stirred at room temperature for 1 hour. The reaction mixture is mixed with ice-water and aqueous sodium bicarbonate solution and extracted with methylene chloride. The organic layer is washed with water, dried over anhydrous sodium sulfate, and concentrated. The residue is chromatographed on a column of silica-gel and eluted with benzene-ethyl acetate (1:1 v/v). The eluate is concentrated, and the resulting residue is crystallized from ethyl acetate-isopropyl ether to give 219 mg of 4-(2,4-dichlorophenyl)-5-(4-fluorophenyl)-2-oxo-4-(1H-1,2,4-triazol-1-yl)methyl-1,3-dioxolane as crystals. m.p. 190°–191° C. Yield: 51.3%

EXAMPLE 17–24

The following starting materials (II) are allowed to react with oxalyl chloride in the same manner as in Example 16 to give the corresponding objective compounds (Ib).

(II)  (Ib)

| Ex. No. | R | $X^1$ | $X^2$ | Az | m.p. (°C.) | Yield (%) |
|---|---|---|---|---|---|---|
| 17A | i-Pr | 4-Cl | H | Tr | 104–105 | 52 |
| B | i-Pr | 4-Cl | H | Tr | 200–201 | 82 |
| 18 | Cl—⌬—Cl | H | H | Tr | 145–146 | 64 |
| 19 | Cl—⌬— | 2-Cl | 4-Cl | Tr | 178–179 | 86 |
| 20 | F—⌬— | 2-Cl | 4-Cl | Im | 209–212 | 77 |
| 21 | F—⌬— | 4-Cl | H | Tr | 176–177 | 83 |
| 22 | Cl—⌬— | 2-Cl | 4-Cl | Im | 238–239 | 51 |
| 23 | Ph | 2-Cl | 4-Cl | Im | 230–232 | 82 |
| 24 | Cl—⌬— | 2-Cl | 4-Cl | Tr | IR(CHCl₃) 1815 cm⁻¹ | 47 |

Note:
(1) Abbreviations in the table have the following meanings.
Im(1H—1,4-imidazol-1-yl), Tr(1H—1,2,4-triazol-1-yl).
(2) Relationship between A and B in Example 17; each is a diastereomer of each other.
(3) Yield in Example 17A means the yield when one diastereomer (m.p. 110–111° C.) of the starting diol is used, and Yield in Example 17B means the yield when another diastereomer (m.p. 149–151° C.) is used.
(4) Relationship between compound in Example 19 and that of Example 24; each is a diastereomer of each other, as in Example 17.

EXAMPLE 25

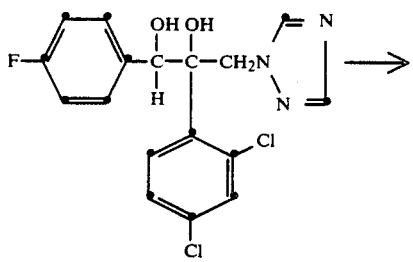

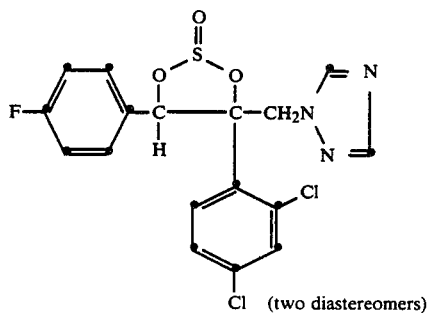

(two diastereomers)

To a solution of 400 mg of 2-(2,4-dichlorophenyl)-1-(4-fluorophenyl)-3-(1H-1,2,4-traizol-1-yl)-1,2-propanediol and 127 mg of triethylamine in 20 ml of dry chloroform is added a solution of 150 mg of thionyl chloride and 1.5 ml of dry chloroform in small portions under ice-cooling, and the mixture is stirred at room temperature for 30 minutes. The reaction mixture is mixed with ice-water and aqueous sodium bicarbonate solution and is extracted with methylene chloride. The organic layer is washed with water, dried over anhydrous sodium sulfate, and concentrated. The residue is chromatographed on a column of silica-gel and eluted with benzene-ethyl acetate (1:1 v/v). The preliminary eluate is concentrated, and the residue is crystallized from ethyl acetate-isopropyl ether to give 158 mg of 4-(2,4-dichlorophenyl)-5-(4-fluorophenyl)-4-(1H-1,2,4-triazol-1-yl)methyl-1,3,2-dioxathiolane-2-oxide as crystals. m.p. 170°–171° C. Yield: 35.3%

Anal. Calcd. (%): (for $C_{17}H_{12}N_3O_3Cl_2SF$): C, 47.68; H, 2.82; N, 9.81; Cl, 16.55; S, 7.49; F, 4.44. Found (%): C, 47.55; H, 2.96; N, 9.84; Cl, 16.51; S, 7.61; F. 4.73.

IR $\nu_{max}^{Nujol}$: 1230, 1170 cm⁻¹.

NMR $\delta^{d6\text{-}DMSO}$:

4.30(d,J=16.5Hz,1H) ⎫
4.98(d,J=16.5Hz,1H) ⎬ —CH₂—

6.45(s,1H,—O—CH⟨), 7.65(s,1H) ⎫
8.27(s,1H) ⎬ triazole H 7.25–8.05(m,7H,arom.H)

The subsequent eluate is concentrated, and the residue is crystallized from methanol to give 134 mg of the diastereomer of the above product as crystals. m.p. 237°–239° C. Yield: 29.9%.

Anal. Calcd. (%): (for $C_{17}H_{12}N_3O_3Cl_2SF$): C, 47.68; H, 2.82; N, 9.81; Cl, 16.55; S, 7.49; F, 4.44. Found (%): C, 47.53; H, 2.96; N, 9.71; Cl, 16.45; S, 7.61; F, 4.67.

IR $\nu_{max}^{Nujol}$: 1215, 985 cm⁻¹.

NMR $\delta^{d6\text{-}DMSO}$:

4.35(d,J=16.5Hz,1H) ⎫
4.82(d,J=16.5Hz,1H) ⎬ —CH₂—

6.75(s,1H,—O—CH)

8.32(s,1H,triazole H)
7.25–7.70(m,8H,arom H and triazole H)

EXAMPLE 26–29

The following starting materials (II) are allowed to react with thionyl chloride in the same manner as in Example 25 to give the corresponding objective compounds (Ic).

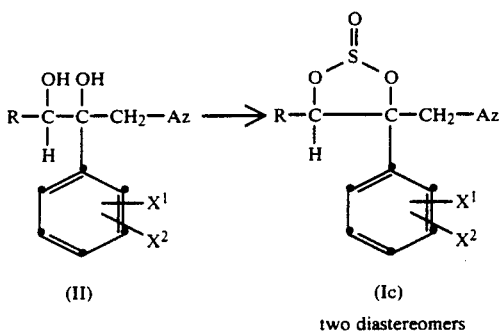

(II) → (Ic)

two diastereomers

| Ex. No. | R | X¹ | X² | Az | m.p. (°C.) | Yield (%) |
|---|---|---|---|---|---|---|
| 26A | i-Pr | 4-Cl | H | Tr | 157–158 | 23 |
| B | i-Pr | 4-Cl | H | Tr | 120–121 | 20 |
| 27A | 2,4-diCl-C₆H₃ | 4-Cl | H | Tr | 163.5–164.5 | 19 |
| B | 2,4-diCl-C₆H₃ | 4-Cl | H | Tr | 108–109 | 28 |
| 28A | Ph | 2-Cl | 4-Cl | Tr | 179–180 | 27 |
| B | Ph | 2-Cl | 4-Cl | Tr | 231–233 | 16 |
| 29A | 4-Cl-C₆H₄ | 2-Cl | 4-Cl | Tr | 187–188 | 4 |
| B | 4-Cl-C₆H₄ | 2-Cl | 4-Cl | Tr | 235–236 | 35 |

EXAMPLE 30

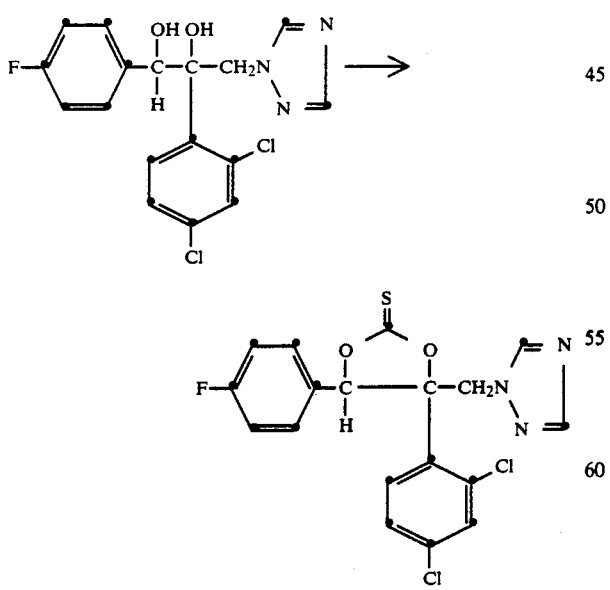

A solution of 500 mg of 2-(2,4-dichlorophenyl)-1-(4-fluorophenyl)-3-(1H-1,2,4-triazol-1-yl)-1,2-propanediol and, 700 mg of 1,1'-thiocarbonyldiimidzole in 10 ml of dry chloroform is heated under reflux for 1 hour. To the reaction mixture is added ice-water, and the mixture is extracted with chloroform. The chloroform layer is washed with water, dried over anhydrous sodium sulfate, and concentrated. The residue is chromatographed on a column of silica-gel and eluted with benzene-ethyl acetate (4:1 v/v). The eluates containing the objective compound are combined and concentrated. The residue is washed with isopropyl ether to give crystalline materials. The crystals are recrystallized from ethyl acetate-isopropyl ether to give 360 mg of 4-(2,4-dichlorophenyl)-5-(4-fluorophenyl)-2-thioxo-4-(1H-1,2,4-triazol-1-yl)methyl-1,3-dioxolane. m.p. 169°–170° C. Yield: 64.9%.

IR $\nu_{max}^{Nujol}$: 1303, 1290 cm$^{-1}$ (C=S).

Anal. Calcd. (%) (for $C_{18}H_{12}N_3O_2Cl_2FS$): C, 50.96; H, 2.85; N, 9.90; Cl, 16.71; F, 4.48; S, 7.56. Found (%): C, 50.91, H, 2.98; N, 9.97; Cl, 16.51; F, 4.77; S, 7.69.

NMR $\delta^{CDCl_3}$ $\left.\begin{array}{l}4.20(d, J=16.5Hz, 1H)\\ 4.97(d, J=16.5Hz, 1H)\end{array}\right\}$ —C$\underline{H_2}$—

6.28(s,1H, —O—C$\underline{H}$—

$\left.\begin{array}{l}7.59(s,1H)\\ 7.98(s,1H)\end{array}\right\}$ triazole H 7.15–7.60(m,7H,arom.H)

EXAMPLE 31

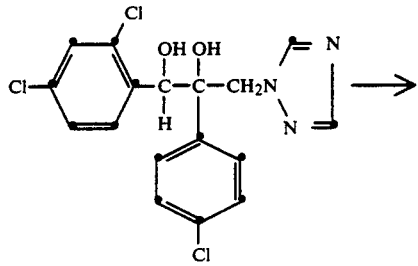

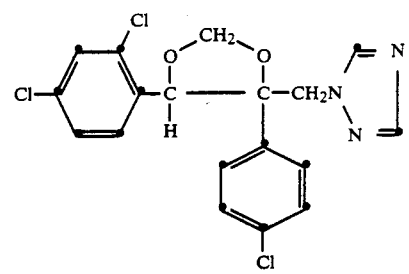

To a solution of 500 mg of 2-(4-chlorophenyl)-1-(2,4-dichlorophenyl)-3-(1H-1,2,4-triazol-1-yl)-1,2-propanediol in 5 ml of dry dimethylformamide is added 180 mg of 50% mineral oil dispersion of sodium hydride under ice cooling. Five minutes later 490 mg of bromochloromethane is added to the mixture, which is allowed to react at a temperature of 50° C. for 1 hour. The reaction mixture is mixed with ice water and shaken with ether. The ethereal layer is washed with water, dried over anhydrous sodium sulfate and concentrated. The residue is chromatographed on a column of silica-gel, which is eluted with 3% methanol-methylene chloride. The eluate is concentrated and the residue is crystallized from ethyl acetate to give 280 mg of 4-(4-chlorophenyl)-5-(2,4-dichlorophenyl)-4-(1H-1,2,4-triazol-1-yl)methyl-1,3-dioxolane as crystals melting at 201° to 203° C. The yield is 54%.

EXAMPLE 32-38

The starting materials (II) are allowed to react with bromochloromethane in the same manner as in Example 31 to give the corresponding objective compounds (Id).

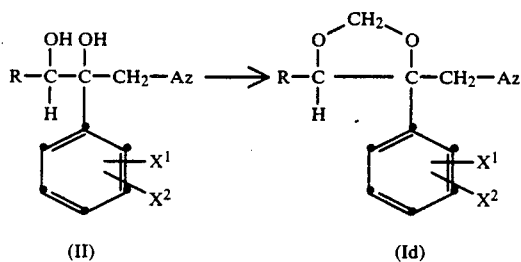

| Ex. No. | R | $X^1$ | $X^2$ | Az | m.p. (°C.) | Yield (%) |
|---|---|---|---|---|---|---|
| 32A | i-Pr | 4-Cl | H | Tr | 90–92 | 74 |
| B | i-Pr | 4-Cl | H | Tr | 139–140 | 37 |
| 33 | Pr | 4-Cl | H | Tr | 123–125 | 37 |
| 34 | F–⌬ | 2-Cl | 4-Cl | Tr | 153–155 | 67 |
| 35 | Cl,Cl–⌬ | H | H | Tr | 146–147 | 82 |
| 36 | F–⌬ | 4-Cl | H | Tr | 130–131 | 63 |
| 37 | Cl–⌬ | 2-Cl | 4-Cl | Im | 144–145 | 52 |
| 38 | Ph | 2-Cl | 4-Cl | Tr | 137–138 | 40 |

EXAMPLE 39

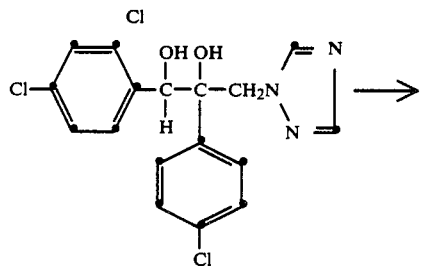

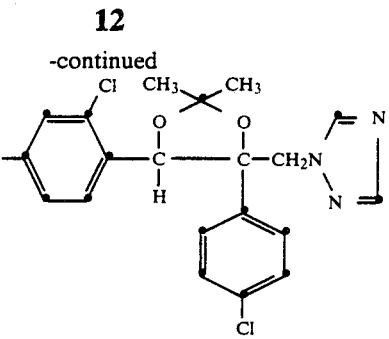

To a solution of 500 mg of 2-(4-chlorophenyl)-1-(2,4-dichlorophenyl)-3-(1H-1,2,4-triazol-1-yl)-1,2-propanediol in a mixture of 20 ml of acetone and 1 ml of dimethylformamide are added 2 ml of 2,2-dimethoxypropane, 100 mg of p-toluenesulfonic acid and about 50 mg of zinc chloride, and the resultant mixture is refluxed for 68 hours. The reaction mixture is poured into cold aqueous sodium hydrogencarbonate solution, and the mixture is shaken with methylene chloride. The organic layer is washed with water, dried over anhydrous sodium sulfate and concentrated. The residue is chromatographed on a column of silica gel, which is eluted with benzene and ethyl acetate (1:1 v/v). The eluate is concentrated and the residue is washed with isopropyl ether to give 110 mg of 4-(4-chlorophenyl)-5-(2,4-dichlorophenyl)-2,2-dimethyl-4-(1H-1,2,4-triazol-1-yl)methyl-1,3-dioxolane as crystals melting at 141° to 142° C. The yield is 20%.

EXAMPLE 40

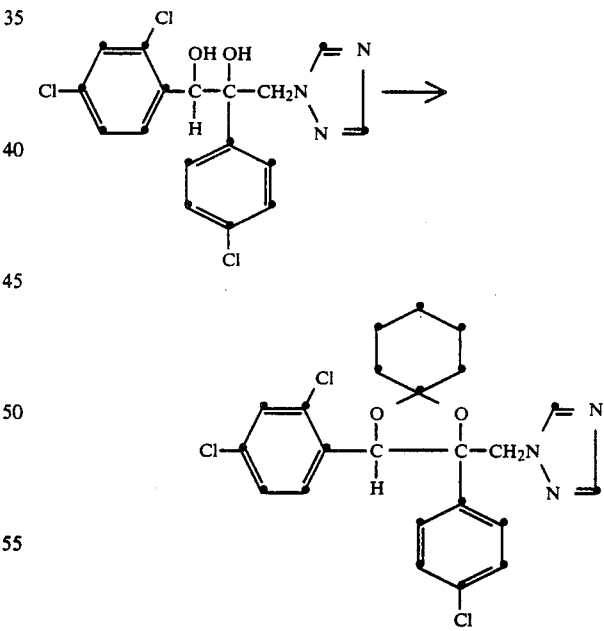

To a solution of 400 mg of 2-(4-chlorophenyl)-1-(2,4-dichlorophenyl)-3-(1H-1,2,4-triazol-1-yl)-1,2-propanediol in a mixture of 2 ml of benzene and 1 ml of dimethylformamide are added 300 mg of cyclohexanone, 2 ml of cyclohexanone dimethyl ketal, 80 mg of p-toluenesulfonic acid and about 40 mg of zinc chloride, and the resultant mixture is refluxed for 68 hours. The reaction mixture is treated as in Example 39, and the resulting product is dissolved in isopropyl ether and mixed with oxalic acid. The precipitate is crystallized from ethyl acetate to give 200 mg of 2-(4-chlorophenyl)-1-(2,4-dichlorohenyl)-3-(1H-1,2,4-triazol-1-yl)-1,2-propanediol cyclohexylidene ketal oxalate as crystals melting at 180° to 181° C. (dec.). The yield is 35%.

EXAMPLE 41

To a solution of 500 mg of 1-(4-chlorophenyl)-2-(2,4-dichlorophenyl)-3-(1H-1,2,4-triazol-1-yl)-1,2-propanediol in 1 ml of dry pyridine is added 300 mg of phenyl chlorocarbonate, and the resultant mixture is allowed to react at room temperature for 18 hours. The reaction mixture is mixed with aqueous sodium hydrogencarbonate solution and shaken with methylene chloride. The organic layer is washed with water, dried over anhydrous sodium sulfate and concentrated. The residue is chromatographed on a column of silica-gel, which is eluted with 2% methanolmethylene chloride. The eluate is concentrated and the residue is crystallized from ethyl acetate-isopropyl ether to give 466 mg of 5-(4-chlorophenyl)-4-(2,4-dichlorophenyl)-2-oxo-4-(1H-1,2,4-triazol-1-yl)methyl-1,3-dioxolane as crystals melting at 178° to 179° C. The yield is 87%.

EXAMPLE 42

The reaction of Example 41 is repeated except that the phenyl chloroformate is replaced by ethyl chlorocarbonate. The resultant product is crystallized from ethyl acetate isopropyl ether to give the same product. The yield is 50%.

The compounds used in the following Experiments are represented by the numbers which correspond to the numbers of the respective Examples.

EXPERIMENT 1

Antimycotic test against Trichophyton asteroides

Minimum Inhibitory Concentration (MIC, $\mu$g/ml) of each test compound against Trichophyton asteroides in vitro antimycotic test is shown below. Sabouraud's dextrose broth* was used as culture medium.
*Totani et al., J. Med. Chem., 24, (12) 1492 (1981)

| Compound Nos. | MIC ($\mu$g/ml) |
|---|---|
| 1 | 0.1 |
| 2 | 3.1 |
| 3 | 0.1 |
| 4 | 0.2 |
| 8 | 3.1 |
| 12 | 1.6 |
| 15 | 3.1 |
| 19 | 0.2 |
| 23 | 0.1 |
| 27B | 0.1 |
| 33 | 0.2 |
| 34 | 0.1 |
| 39 | 0.8 |

EXPERIMENT 2

Test on inhibition against formation of the pseudohyphae in Candida albicans

To Eagle MEN broth (Nissan 2, Nissui Seiyaku Co., Ltd.) was added 20% bovine serum and inoculated Candida albicans KE-2 yeast cells at rate of $1 \times 10^6$ cells/ml (final inoculum size), and each test compound was added thereto in two-fold serial dilution method. After termination of cultivation at 37° C. for 18 hours, each organism of the serial dilution was smeared and fixed on a slide glass and stained by Giemsa's staining, and occurrence of the pseudohyphae was observed under a microscope. Minimum concentration which could inhibit the formation of pseudohyphae was regarded as the inhibitory concentration of the compound against pseudohyphae formation.

| Compound Nos. | Inhibitory concentration against pseudohypae formation ($\mu$g/ml) |
|---|---|
| 1 | 0.31 |
| 2 | 0.63 |
| 5 | 0.63 |
| 7 | 0.31 |
| 11 | 1.25 |
| 15 | 0.63 |
| 19 | 0.04 |
| 23 | 0.16 |
| 27B | 0.02 |
| 33 | 0.16 |
| 34 | 0.31 |
| 39 | 5.00 |

EXPERIMENT 3

Therapeutic effect against experimental candidasis in mice

Candida albicans KE-2 was cultured in a Sabouraud's dextrose agar at 28° C. for 48 hours, and the resulting culture was suspended in the Sabouraud's dextrose broth. The resulting cells ($5 \times 10^5$) were intravenously administered at the tail of Jcl-ICR female mice (4 weeks age, body weight: 18–20 g). Each test compound suspended in 2% gum-arabic was orally administered at a dose of 25 mg/Kg twice per day for 5 days; on the first day, the test compound is administered twice, i.e., immediately after the infection and 2 hours later; on the second day or later, 24 hours after the administration of the previous day respectively. After the infection, no test compound was administered to a control group. Eight mice were employed in the control group and the test groups to which the test compound was administered The therapuetic effect was evaluated on the survival rate at the 15th day from the day of infection; the result is shown below.

| Compound No. | Survival rate (%) |
|---|---|
| 1 | 87.5 |
| 2 | 100 |
| 5 | 100 |
| 19 | 86 |
| 27B | 75 |
| Control | 0 |

What is claimed is:
1. A compound of the formula

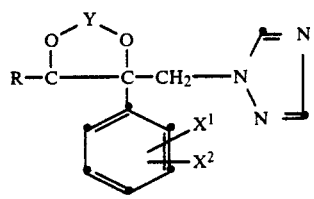

wherein

R is $C_1$-$C_5$ alkyl or phenyl optionally substituted by 1 to 3 members selected from halogen, $C_1$-$C_5$ alkyl, and $C_1$-$C_5$ alkoxy;

$X^1$ and $X^2$ each is hydrogen, halogen, $C_1$-$C_5$ alkyl, $C_1$-$C_5$ alkoxy; and Y is C=O, C=S or C=O, or an acid addition salt thereof.

2. A compound according to claim 1, in which R is $C_3$-$C_4$ alkyl or phenyl substituted by 1 or 2 halogen atoms, at least one of $X^1$ and $X^2$ is halogen, and Y is C=O, C=S or S=O.

3. A compound according to claim 1, namely 4-(2,4-dichlorophenyl)-5-(4-fluorophenyl)-2-oxo-4-(1H-1,2,4-triazol-1-yl)methyl-1,3-dioxolane.

4. A compound according to claim 1, namely (4-(2,4-dichlorophenyl)-5-isopropyl-2-oxo-4-(1H-1,2,4-triazol-1-yl)methyl-1,3-dioxolane.

5. A compound according to claim 1, namely 4-(4-chlorophenyl)-5-(2,4-dichlorophenyl)-2-oxo-4-(1H-1,2,4-triazol-1-yl)methyl-1,3-dioxolane.

6. A compound according to claim 1, namley 5-(4-chlorophenyl)-4-(2,4-dichlorophenyl)-2-thioxo-4-(1H-1,2,4-triazol-1-yl)methyl-1,3-dioxolane.

7. A compound according to claim 1, namely 4-(4-chlorophenyl)-5-(2,4-dichlorophenyl)-2-thioxo-4-(1H-1,2,4-triazol-1-yl)methyl-1,3-dioxolane.

8. An antimycotic composition which comprises an antimycotically effective amount of a compound or a salt thereof according to claim 1 with one or more carriers, diluents and/or excipients.

* * * * *